(12) United States Patent
D'Alessio et al.

(10) Patent No.: US 6,478,191 B1
(45) Date of Patent: Nov. 12, 2002

(54) APPLICATOR WITH PROTECTIVE BARRIER

(75) Inventors: Keith R. D'Alessio, Cary, NC (US); Andres Rivera, Wake Forest, NC (US); Anthony S. Voiers, Raleigh, NC (US); Joe B. Barefoot, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 10/012,441

(22) Filed: Dec. 12, 2001

Related U.S. Application Data (60) Division of application No. 09/447,045, filed on Nov. 23, 1999, now Pat. No. 6,340,097, which is a continuation-in-part of application No. 09/176,889, filed on Oct. 22, 1998, now abandoned.

(51) Int. Cl.[7] .............................................. B65D 37/00
(52) U.S. Cl. ................ 222/129; 215/12.2; 215/DIG. 6; 225/93
(58) Field of Search .......................... 222/129; 225/93; 215/12.2, DIG. 6

(56) References Cited

U.S. PATENT DOCUMENTS

| | | | |
|---|---|---|---|
| 3,658,719 A | * | 4/1972 | McConnaughey ....... 73/170.04 |
| 3,720,341 A | * | 3/1973 | Greenfield et al. ............. 215/6 |
| 3,856,142 A | * | 12/1974 | Vessalo ...................... 206/530 |
| 3,877,969 A | | 4/1975 | Tatsumi et al. ................ 225/93 |
| 3,881,634 A | | 5/1975 | Thrun ............................ 222/3 |
| 3,889,031 A | | 6/1975 | Tatsumi et al. ............. 428/216 |
| 3,913,733 A | | 10/1975 | Flesch et al. ................ 206/219 |
| 3,964,643 A | | 6/1976 | Morane et al. .............. 222/145 |
| 4,099,638 A | | 7/1978 | Tatsumi et al. ................ 428/35 |
| 4,304,869 A | | 12/1981 | Dyke ........................ 435/296 |
| 4,340,670 A | | 7/1982 | Mennen ...................... 435/25 |
| 4,345,028 A | | 8/1982 | Nelson et al. | 
| 4,581,093 A | * | 4/1986 | Noyes et al. ............. 156/307.3 |
| 4,624,725 A | * | 11/1986 | Lamm et al. ................ 156/310 |
| 4,732,850 A | | 3/1988 | Brown et al. |
| 4,826,025 A | | 5/1989 | Abiko et al. ................... 215/49 |
| 5,129,566 A | | 7/1992 | Ogden et al. |
| 5,133,458 A | * | 7/1992 | Miller ........................ 206/530 |
| 5,154,320 A | | 10/1992 | Bolduc |
| 5,256,537 A | | 10/1993 | Phillips et al. |
| 5,370,938 A | * | 12/1994 | White et al. ................ 428/458 |
| 5,628,353 A | | 5/1997 | Ruther |
| 5,690,958 A | | 11/1997 | McGrath |
| 5,948,366 A | | 9/1999 | Ruther |
| 6,039,488 A | * | 3/2000 | Krawczyk et al. .......... 401/132 |

FOREIGN PATENT DOCUMENTS

WO WO 96/40797 12/1996

OTHER PUBLICATIONS

James Alexander Corporation Brochure on Ampoule-Based Products (Date Unknown).

\* cited by examiner

Primary Examiner—J. Casimer Jacyna
(74) Attorney, Agent, or Firm—Oliff & Berridge, PLC (57) ABSTRACT

An applicator for dispensing compositions includes a crushable ampoule covered with a barrier material that serves as a protective barrier. The applicator can also include a body made of a flexible material that holds at least one crushable ampoule. The protective barrier protects the user's fingers from puncture by shards created during breakage of the crushable ampoule.

11 Claims, 7 Drawing Sheets

APPLICATOR WITH PROTECTIVE BARRIER

This application is a Division of U.S. application Ser. No. 09/447,045 filed Nov. 23, 1999, U.S. Pat. No. 6,340,097 which is a Continuation-In-Part of U.S. application Ser. No. 09/176,889 filed Oct. 22, 1998, now abandoned the entire contents of which are hereby incorporated by reference.

BACKGROUND OF THE INVENTION

1. Field of the Invention

This invention relates to applicators or dispensers which comprise crushable ampoules, preferably housed within flexible tubular containers. The invention also relates to methods of producing such applicators or dispensers.

2. Description of Related Art

Applicators comprising crushable glass ampoules housed within flexible applicator bodies are known in the art. Examples of such applicators comprise flexible tubular elements that have at least one end permanently closed. The other end can be frangibly closed or remain open to the environment. The crushable glass ampoules are typically sealed and contain a composition to be dispensed. Applicator tips are sometimes fixed to the open end to aid in the application of the composition contained within the ampoule. This type of applicator is useful for multiple applications including use as air fresheners, use in dye marking, and use in pregnancy test kits, as well as for dispensing medical solutions, dental products, health and beauty aids, adhesives, and other compositions. To use the dispenser, the flexible applicator tube is squeezed at the area where the glass ampoule is located. Sufficient force is applied by a user's fingers to break the glass ampoule, releasing the composition contained within. The composition is then applied through, or otherwise allowed to exit, the open end (i.e., the end with the applicator tip).

One drawback to such applicators is the possibility of a glass shard from the broken ampoule piercing the flexible tube and entering the user's hand during crushing and dispensing. Upon crushing of the glass ampoule, multiple small sharp glass shards are created. Among the glass shards created during breakage of the glass, shards having a length sufficient to transect the flexible applicator tube are created. A certain percentage of these shards become reoriented such that they are perpendicular to the length of the applicator tube (i.e., with their longitudinal axis oriented toward the user's finger(s)). The force applied during crushing and dispensing can be sufficient to force at least some of these reoriented shards through the flexible tube and into the user's finger(s).

This disadvantage is overcome in some applicators by a cardboard overcap that can be placed around the applicator body to protect the user's fingers during crushing of the ampoule. Such an applicator, consisting of a glass ampoule, a plastic butyrate tube, and a cardboard overcap, is sold by the James Alexander Corporation of Blairstown, N.J. In operation, prior to crushing of the ampoule, the cardboard sleeve is slid over the ampoule and the user crushes the ampoule by squeezing the ampoule with the user's fingers through the cardboard sleeve. However, this solution does not eliminate the production of reoriented glass shards, and is subject to a certain failure rate due to the reoriented shards puncturing the overcap along with the flexible tube. It also requires a separate part that makes the dispenser a two-handed operation to place the cardboard cover on the applicator. Moreover, as the sleeve is opaque, one cannot see whether the ampoule has been properly crushed during use without removal of the sleeve.

Commonly assigned U.S. Pat. No. 5,928,611 (previously published under PCT Application No. WO 96/40797), the disclosure of which is hereby incorporated in its entirety, discloses an applicator for dispensing polymerizable or cross-linkable monomer compositions. The applicator comprises an applicator body that holds a crushable ampoule. The crushable ampoule contains the monomer composition that is to be dispensed. The applicator can further comprise an applicator tip. This applicator, like those described above, does not disclose means to avoid reorientation of glass shards.

Other methods for protecting a user's hands during crushing of a glass ampoule are disclosed in U.S. Pat. No. 5,690,958 to McGrath. McGrath discloses a unit dose applicator for dispensing chlorhexadine gluconate (CHG). The applicator may be an elongated cylindrical glass vial or ampoule that is housed within an elongated cylindrical, flexible, synthetic resin cover of a size to fully encase the vial. A porous applicator swab is fitted within one end of the applicator cover, and extends outward therefrom. The cover is disclosed as being a protective cover that protects the user's hand from glass shards created during crushing of the unit dose glass container. However, McGrath does not disclose or claim the use of his applicator to dispense anything except CHG and has the disadvantage that reoriented glass shards can puncture the protective resin cover.

U.S. Pat. No. 4,826,025 to Abiko et al. discloses an ampoule package that is designed to be precisely cut at a constriction between upper and lower sections of the package. A heat-shrink film is provided over the constriction part to prevent scatter of fine particles of glass formed by the cutting of the constriction. Such an ampoule is not designed to be crushed by a user's fingers. Thus Abiko is not concerned with problems of reoriented glass shards that could puncture a user's fingers during the crushing.

Similarly, it is known to coat glass bottles with coating materials to improve resistance to breaking. For example, U.S. Pat. Nos. 3,877,969, 3,889,013, and 4,099,638 to Tatsumi et al. disclose coating the surface of glass bottles with two different kinds of coating materials in a specific sequence. The coating materials include an olefin copolymer containing OH and/or COOH groups in its molecule. The coating also includes a polyisocyanate or a mixture of a polyisocyanate and a polyol or a thermoplastic polyurethane. These methods are not disclosed as having applicability to, and in fact are conceptually opposed to, glass containers that are designed to be broken, such as glass ampoules broken by finger pressure. Rather, they are intended to resist or prevent breakage.

SUMMARY OF THE INVENTION

Thus, there is a need for an applicator comprising a crushable ampoule that can be used without fear of puncture of the skin during crushing. The present invention satisfies that need by providing a protective barrier material over the surface of the crushable ampoule. The protective barrier material not only protects a user's hand from puncture with shards created during crushing of the ampoule, but it can be used and incorporated in an applicator in a convenient and economical manner.

The invention provides an applicator or dispenser, which comprises a crushable ampoule, containing a composition to be dispensed, that is covered or coated by a resistant barrier material. The applicator can further comprise a hollow applicator body made of a flexible and deformable material. The applicator body is of a generally tubular shape, having an end that is permanently closed and another end that can either be closed (sealed) or open to the environment. At least one crushable ampoule is contained within the lumen of the applicator body. Each crushable ampoule is sealed and can contain a composition that is to be delivered or applied to a site or reacted with another material in the applicator. Disposed over a surface of each crushable ampoule is a material that acts as a barrier against formation of reoriented glass shards upon crushing of the ampoule. The barrier material can be applied to either or both of the interior or exterior surface of the crushable ampoule, applied between the ampoule and applicator body, and/or applied to the exterior of the applicator body. It may be applied to the entire interior and/or exterior surface, or may be applied only to a selected portion of such surface. In the latter case, it is preferably applied to a portion, such as a central portion, that is most susceptible to crushing and shard reorientation.

According to one aspect of the invention, the barrier material protects a container body, and thus a user's fingers, from puncture by reoriented glass shards during crushing of the ampoule by the barrier material being in contact with both the flexible tube of the applicator body and the crushable ampoule. The contact may be through affixing of the barrier material to the ampoule or by adhesive contact.

According to another aspect of the invention, the barrier material is in contact with an interior surface of the ampoule. Again, the contact may be through affixing or adhering of the barrier material to the ampoule.

According to a further aspect of the invention, the barrier material may be a resistant polymeric layer, such as a MYLAR® polyester film, affixed to the exterior of the ampoule or applicator body.

According to yet another aspect of the invention, the barrier material may be the combination of an adhesive layer and a label adhered to an exterior surface of the applicator body.

According to yet a further aspect of the invention, the barrier material may be a plastic composition coated on the exterior of the ampoule or applicator body.

According to each of the above-described aspects, the barrier material is thin enough and/or flexible enough to allow crushing of the ampoule by an average person's finger pressure.

The invention also provides a method of making an applicator or dispenser. The method comprises applying a barrier material to a surface of one of the crushable ampoule and the applicator body. The method can further comprise inserting the coated crushable ampoule into the applicator body.

Alternatively, the method may include insertion of the barrier material onto an interior surface of the applicator body before insertion of the ampoule within a lumen of the applicator body. Upon insertion of the ampoule, the barrier material is spread over a substantial surface of the ampoule to provide resistance to reorientation and/or puncture by glass shards.

The method may also include application of a barrier material to the exterior surface of the ampoule before insertion of the ampoule within the lumen of the container body.

The barrier material may be an adhesive that is coextruded with the flexible material making up the applicator body.

When the barrier material is adhered to a surface of the crushable ampoule, the number of reoriented shards generated during crushing of the ampoule can be reduced or eliminated. Thus few, if any, reoriented shards that can transect the applicator and puncture the user's skin are created. This is because the shards, when created, are trapped by the adhered barrier material in the orientation in which they were created. In this manner, puncturing of the user's fingers by reoriented shards is reduced or eliminated, and the safety of the applicator is improved. Furthermore, because a wide variety of barrier materials can be used, which are generally inexpensive, the barrier material can be incorporated without a significant increase in the cost of producing the applicator. In addition, the applicator can be used in a single, one-handed operation, and does not inhibit the view of the applicator. Moreover, when the barrier material is affixed or adhered in place, there is no possibility that the sleeve may slide from a desired area to be protected.

Thus, in some embodiments, the barrier material may form a layer or coating that is affixed to or adheres tightly to the material from which the ampoule is made. During crushing of the ampoule, the barrier material in these embodiments continue to be affixed to or adhered to the material of the ampoule, and, to a great extent, to itself. Thus, the three dimensional structure of the barrier material is not completely destroyed during the crushing process. In other words, although the ampoule is crushed, the general shape of the ampoule is retained by the barrier material on the ampoule. Because the barrier material remains affixed or adhered to the shards of the ampoule and generally retains its original shape, the production of reoriented shards is greatly reduced. Furthermore, at least one area of the ampoule is preferably left uncovered so that the composition within the ampoule can escape upon crushing of the ampoule. The uncovered area can be provided as one relatively large area, for example at one end of the ampoule, or can be provided as many relatively small areas dispersed over a specific area or over the entire ampoule. The uncovered area can be any shape or size as long as the protective function of the barrier material is not compromised.

It is often preferable for the barrier material to have adhesive properties so that it can be directly adhered to the material comprising the ampoule. If the barrier material is not adhered to (or sufficiently affixed to) this ampoule material, then, upon crushing of the ampoule, reorientation of shards can occur because they are not trapped in their original orientation. In embodiments where the barrier material is an adhesive, the adhesive material itself does not provide a sufficient physical barrier to the shards, as it is easily punctured by reoriented shards. It is the substantial blocking of reorientation of the shards by the adhesive in these embodiments that provides the protective function of the present invention.

In other aspects of the invention, the barrier material may be affixed to the ampoule and serve to partially prevent reorientation and may also be formed of a material that provides a physical barrier to penetration by shards of glass.

Further, when the barrier material is applied to the exterior surface of the ampoule, entrapment of the shards by the barrier material provides an added level of protection by providing a barrier against shards that failed to be adhered by the barrier material. For example, during crushing, a certain, although small, portion of the shards will not be adhered to by the adhesive barrier material. This is especially true for shards that are created solely from ampoule material at surfaces not covered by the adhesive barrier material. A certain percentage of these free shards can become reoriented. However, the shards entrapped by the adhesive form a relatively thick, strong layer that can stop the reoriented shards from passing through and into the user's fingers. Thus, the shards themselves provide added protection and serve as a protective physical barrier in such embodiment, allowing the use of an adhesive with weak physical barrier properties.

The applicator body can hold one crushable ampoule containing a composition to be dispensed and/or reacted, or can contain multiple crushable ampoules, each containing a composition to be dispensed and/or reacted. When the applicator comprises multiple ampoules, each ampoule can hold either the same composition or a different composition. Included is the situation where multiple ampoules contain the same composition while other ampoules contain different composition(s). For example, the applicator can comprise two crushable ampoules. The first ampoule holds the first part of a two-part adhesive and the second ampoule holds the second part of a two-part adhesive, such as a two-part epoxy adhesive. Furthermore, in embodiments where multiple ampoules are included, at least one ampoule can be contained within another.

Although the invention is further described with respect to preferred applicators comprising an applicator body that contains a coated crushable glass ampoule, the invention also encompasses applicators comprising the adhesive-coated ampoule alone.

DETAILED DESCRIPTION OF PREFERRED EMBODIMENTS

Figure 1:
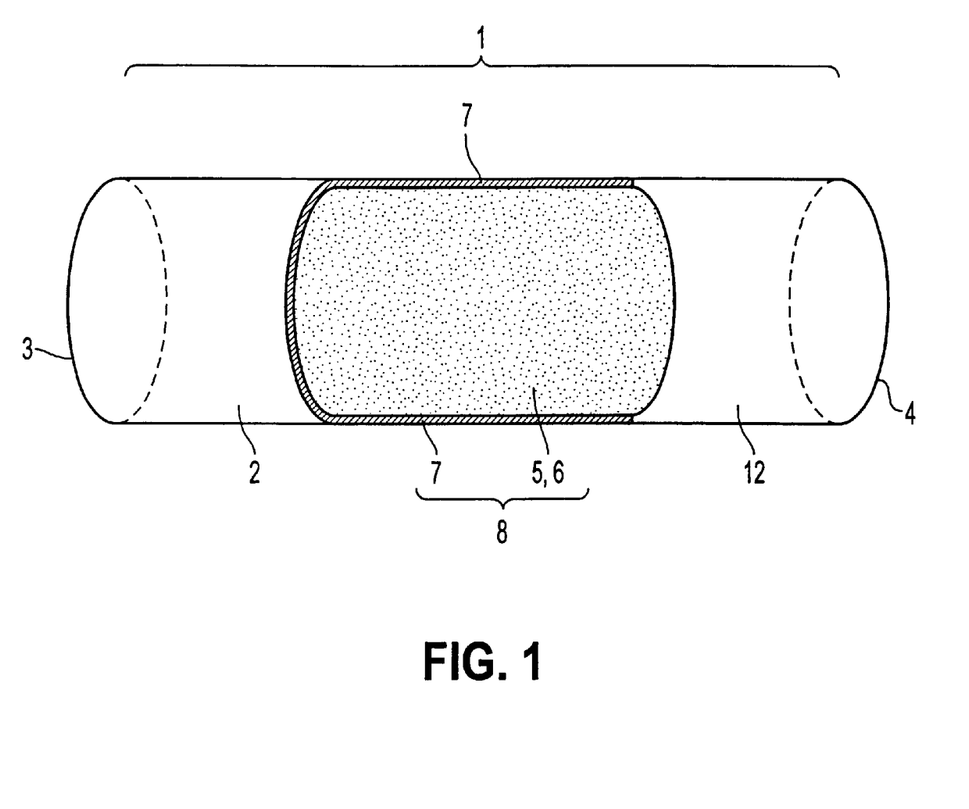
FIG. 1 depicts an applicator of the present invention.

With reference to FIG. 1, the present invention provides an applicator 1 comprising an applicator body 2, which is formed generally in the shape of a tube having a closed end 3, an open end 4, and a hollow interior lumen 12, which holds a crushable or frangible ampoule 5. The ampoule contains a composition 6, which is to be dispensed from the applicator. According to one aspect of the invention, a barrier material 7 is disposed between the interior surface of the applicator body and the exterior surface of the crushable ampoule. Although the present invention is extremely useful in conjunction with ampoules made of glass, ampoules made of other brittle materials can create reoriented shards and are encompassed by the present invention. Further, although FIG. 1 depicts a preferred embodiment wherein the ampoule has an outer diameter that is fractionally smaller than the inner diameter of the applicator body, such a relationship is not a critical feature of the invention. Thus, an applicator having a crushable ampoule that has a significantly smaller outer diameter than the inner diameter of the applicator tube is encompassed by the present invention. Furthermore, the ampoule need not be in the shape of a tube, but can be in any chosen shape, including oval, round, etc.

Alternately, the barrier material can be disposed on the interior surface of the crushable ampoule. Layering or coating the barrier material on the interior surface of the crushable ampoule provides the same benefits as coating the exterior surface of the crushable ampoule. However, coating the interior surface is not as convenient and economical, and is thus an embodiment of the invention that is not as highly preferred in many cases.

Figure 2:
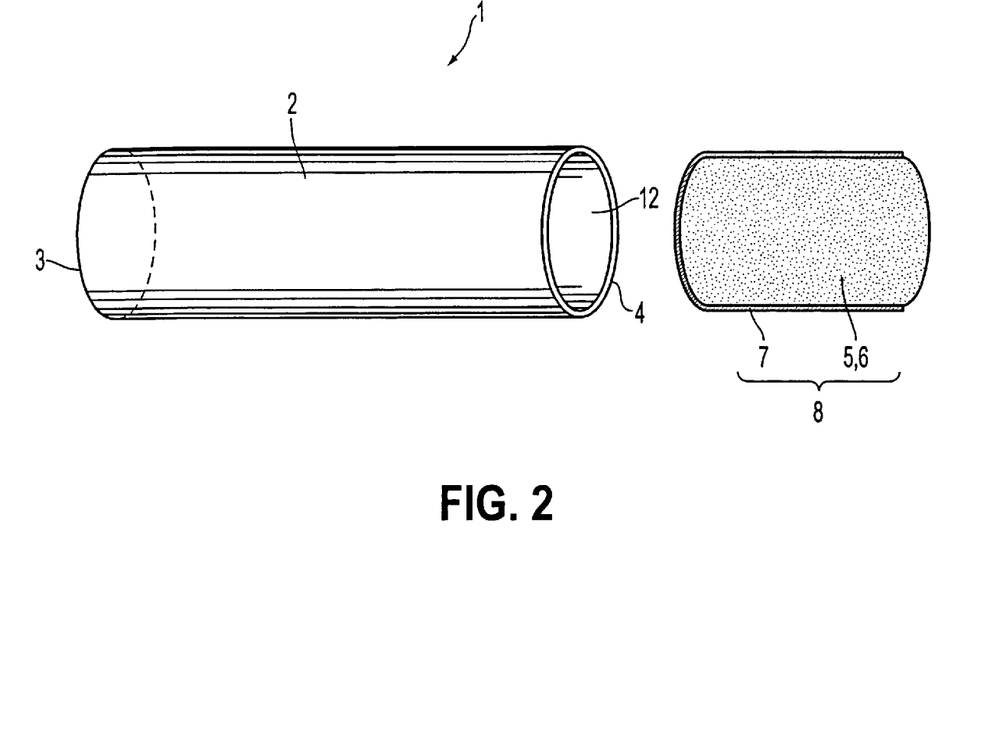
FIG. 2 is an exploded view of one embodiment of the applicator of FIG. 1, depicting the barrier material disposed on the exterior surface of the crushable ampoule.

As depicted in FIG. 2, the barrier material 7 is disposed on the exterior surface of the crushable ampoule 5. The barrier material is applied to the ampoule prior to inserting the ampoule into the hollow interior area 12 of the applicator body 2. The barrier material 7 may be an adhesive. In such an embodiment, sufficient adhesive is applied to the surface to coat the surface at least over the central portion 8 of the ampoule. As used herein, the central portion of the ampoule is that portion of the ampoule that is covered by the user's fingers when the applicator is in use. Thus, the central portion of the ampoule includes that portion of the ampoule where crushing force is applied, as well as that portion of the ampoule where force is applied during dispensing of the composition 6. The amount of adhesive barrier material applied to the ampoule is preferably sufficient to completely cover the central portion, although small gaps in coverage may be permitted. This permits the adhesive to adhere to the entire surface of the ampoule to which force is applied so that reorientation of shards is minimized at these areas. Although the adhesive barrier material need not be applied to those portions of the ampoule that are not likely to be crushed, or that are not likely to be between the user's fingers during operation, it is preferred that these areas be covered as well.

In embodiments, the adhesive barrier material is applied to the exterior surface of the ampoule and allowed to cure (or set) prior to inserting the ampoule into the applicator body. As used herein, the terms "cured" adhesives are those encompassed by pressure-sensitive adhesives that are in a state ready for use, hot-melt adhesives that are in the solid state, and reactive adhesives that have undergone the reaction required to generate the desired properties of the adhesive (for example, polymerizable adhesive materials that have polymerized).

In other embodiments, the adhesive barrier material is applied and the ampoule is inserted into the applicator body before the adhesive cures. The adhesive is then allowed to cure while the ampoule is within the applicator body. In embodiments where an ampoule is used that has an outer diameter that is fractionally smaller than the inner diameter of the applicator tube, the adhesive can adhere to both the exterior surface of the ampoule and the interior surface of the applicator tube upon curing. Such dual adhesion aids in anchoring of the ampoule at a specific point within the applicator and can be desirable when the length of the ampoule is significantly shorter than the length of the applicator body.

Alternatively, the barrier material 7 can be of a polymeric substance, such as a MYLAR® polyester film or a plastic coating, that is affixed to the ampoule by a friction fit, mechanical bond, as part of a coating or dipping process or by other common methods of affixing or coating. By affixing or adhering the barrier material to the ampoule, the amount of reoriented shards can be reduced. Also in this embodiment, the film coating thickness can be selected to remain flexible, while providing an improvement in physical barrier properties over the adhesive embodiment.

Figure 3:
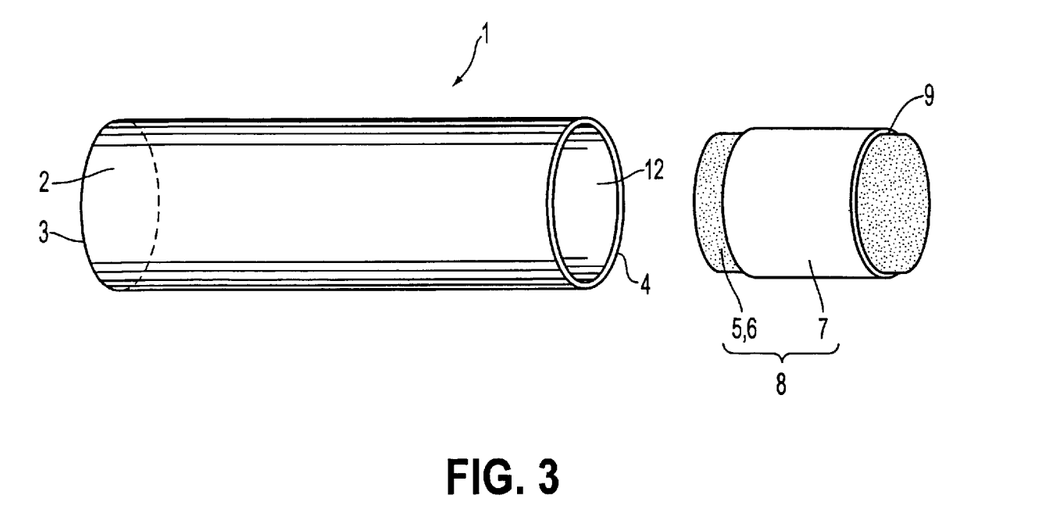
FIG. 3 is an exploded view of one embodiment of the applicator of FIG. 1, depicting the barrier material disposed on the exterior surface of the crushable ampoule as part of a label.

In an embodiment depicted in FIG. 3, the adhesive barrier material 7 that is applied to the exterior surface of the ampoule is an adhesive that is also used to adhere an adhesive tape or label 9 to the ampoule. In this embodiment, the adhesive serves the purpose of holding the shards in their original orientation upon crushing of the ampoule as well as permitting the tape, a label, or the like to be affixed to the ampoule. For example, the label can be any of the known adhesive-backed labels commonly used in the medical, industrial, and business industries, such as polyester labels and the like. The label can be used to indicate the identity of the composition within the ampoule, the date it was filled, the expiration date, or any other relevant information.

Figure 4:
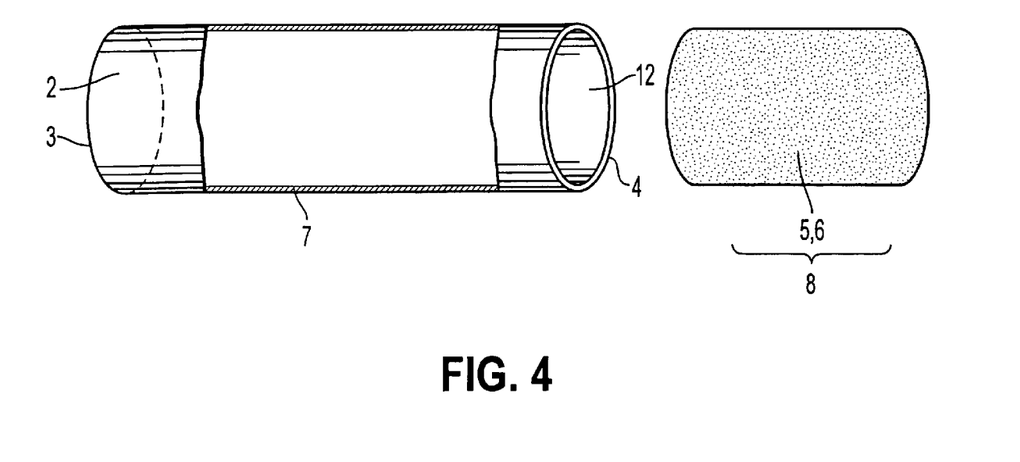
FIG. 4 is an exploded view of one embodiment of the applicator of FIG. 1, depicting the barrier material disposed on the interior surface of the applicator tube.

In an embodiment depicted in FIG. 4, the interior surface of the applicator body 2 is coated with a barrier material 7, which may be an adhesive or a polymeric layer as described above, affixed to the applicator body. In this embodiment, when an adhesive is used, the crushable glass ampoule may be inserted before the adhesive cures. The adhesive adheres to the interior surface of the applicator body and the exterior surface of at least the central portion 8 of the crushable ampoule and provides a protective barrier. In this embodiment, the uncured adhesive contacts and preferably completely covers at least the central portion 8 of the ampoule and is allowed to cure while covering this area.

Figure 5:
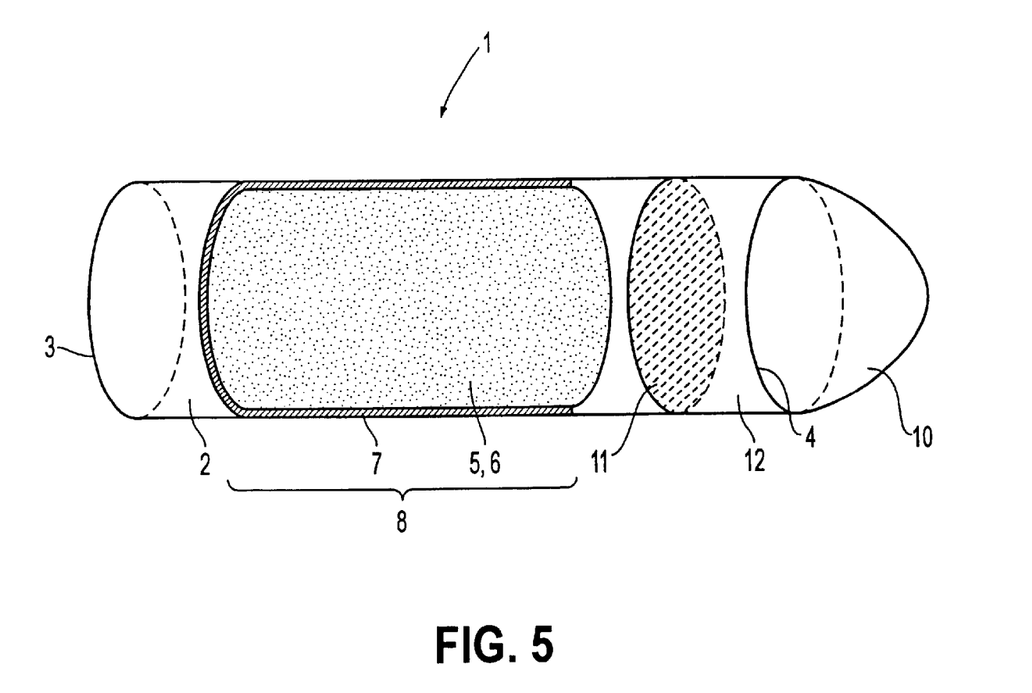
FIG. 5 depicts a preferred embodiment of the present invention.

In preferred embodiments of the invention, the applicator can comprise elements other than the applicator body and ampoule. As shown in FIG. 5, for example, an applicator tip 10 is provided on the applicator 1. The applicator tip can have a variety of suitable shapes, including, but not limited to, conical, cylindrical, chisel or polygonal shapes. The length and size of the tip can be varied depending on various application parameters. The tip may be detachable from the applicator body, or may be an integral part of the applicator. The tip further may be in the form of a nozzle for atomizing liquid solutions. The tip can be composed of any of a variety of materials including polymerized materials such as plastics, foams, rubber, thermosets, films, or membranes. Additionally, the applicator tip may be composed of materials such as metal, glass, paper, ceramics, cardboard, and the like. The applicator tip material may be porous, absorbent, or adsorbent in nature to enhance and facilitate application of the composition within the ampoule. In general, the only limitation on the materials used to fabricate the tip is that the tip must be sufficiently compatible with the composition to be dispensed that undesirable effects on the composition do not prevail during contact of the composition with the tip.

Further, as shown in FIG. 5, the applicator can comprise a screen or filter 11 between the crushable ampoule and the open end 4 of the applicator body 2. Although it should not be necessary in the applicator of the present invention, it can be incorporated to stop any shards that are released upon breaking of the ampoule from exiting the applicator along with the composition being applied.

Figure 6A:
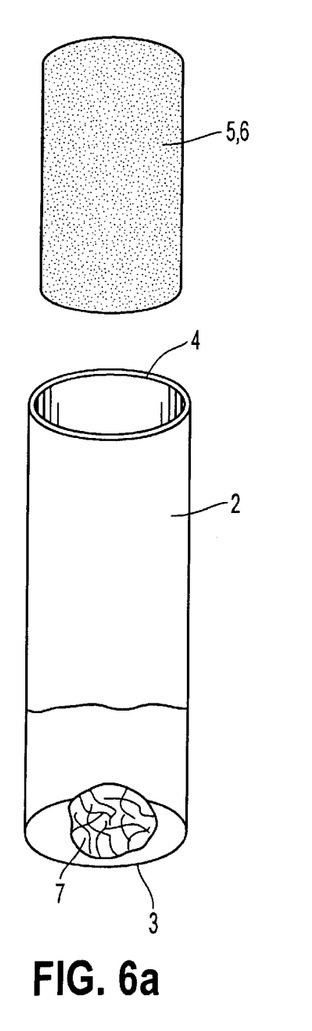
FIGS. 6a–6c depict a method of making an applicator according to one embodiment of the present invention.
Figure 6B:
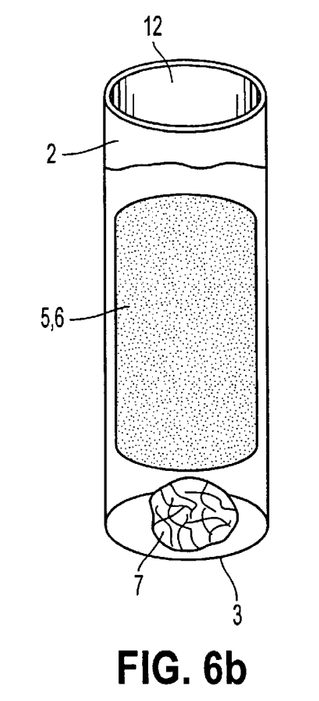
Figure 6C:
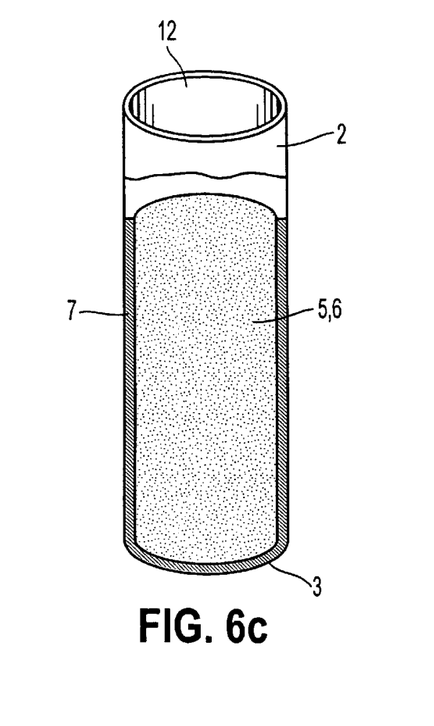

As depicted in FIGS. 6a–6c, both the interior surface of the applicator body and the exterior surface of the crushable ampoule can be coated with the material at the same time. As shown in FIG. 6a, uncured adhesive barrier material 7 is placed within the closed end 3 of the applicator body 2. As shown in FIG. 6b, the crushable ampoule 5, which has an outer diameter that is fractionally smaller than the inner diameter of the applicator body, is then inserted through the open end 4 into the applicator body 2. In this manner, when the ampoule is inserted into the hollow inner area 12 of the body 2, and forced to the bottom of the tube, the adhesive within the tube is displaced and forced into the space between the ampoule and the body (FIG. 6c). In this embodiment, enough adhesive is originally placed within the applicator body so that displacement of the adhesive results in coverage of at least the central portion of the ampoule. The adhesive is then permitted to cure and adhere to both surfaces.

Figure 7:
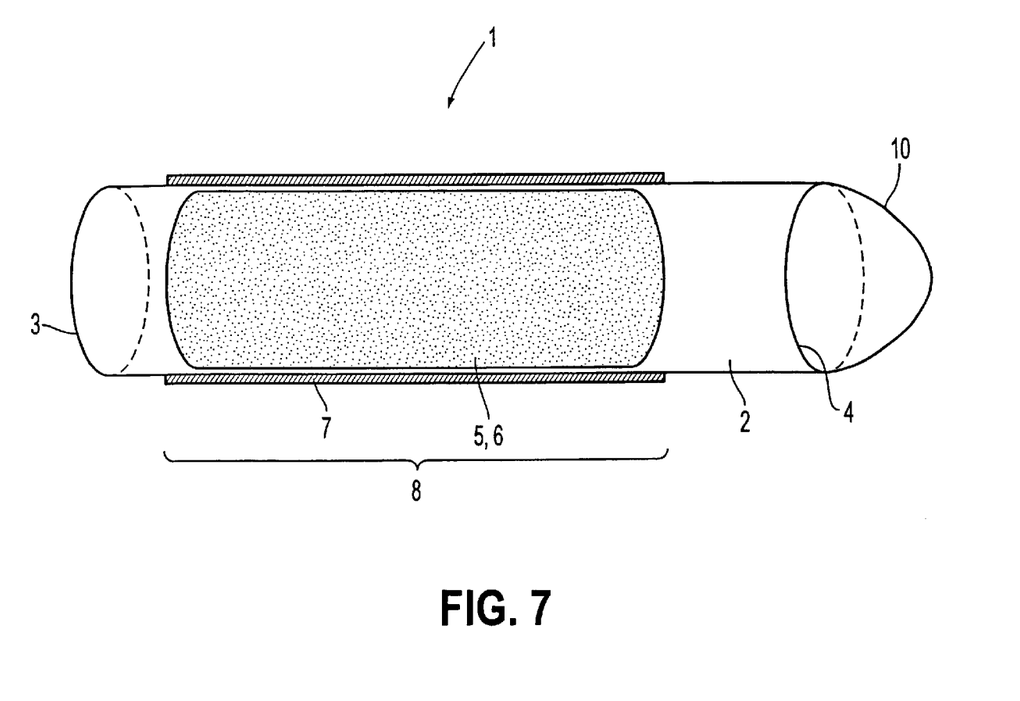
FIG. 7 is a view of one embodiment of the invention in which the barrier material is a polymeric film affixed to the exterior of the applicator tube.

In an embodiment depicted in FIG. 7, a barrier material 7 is affixed to an exterior surface of the applicator body 2. The barrier material 7 preferably covers at least the central portion 8 of ampoule 6 to protect a user's fingers from shards during use of the applicator (forced breakage of the ampoule 6). A suitable barrier material 7 is a polymeric layer, such as a MYLAR® polyester film, which is preferably clear to allow viewing of the contents of ampoule 6, while still providing a protective barrier that is affixed to the applicator to cover the critical central area of the ampoule 6 where breakage of ampoule 6 is to be induced by a user's fingers applying a suitable pressure. As in the FIG. 5 embodiment, the applicator I may be provided with a suitable applicator tip 10 on open end 4 opposite closed end 3. The barrier material 7 may include indicia or other markings such that the protective barrier material can also serve as an applicator label. The barrier material 7 can have a wide latitude of sizes and thicknesses so long as at least open end 4 is left uncovered to allow exiting of the contents of ampoule 6 and the barrier material 7 is sufficiently flexible or compressible to allow breakage of ampoule 6 by application of finger pressure or its equivalent acting through the barrier material 7 to be transmitted to the ampoule 6 within.

The material that comprises the flexible applicator body is any material that is flexible, and allows forces generated on the outside of the body to be transmitted to the ampoule within. The material can be any material that is sufficiently compatible with the barrier material and/or composition to be applied such that undesirable effects on the composition to be dispensed are not seen as a result of contact between the applicator body material and the composition. In preferred embodiments, the flexible material is transparent or translucent, allowing the user to see inside the tube and view the location and contents of the ampoule. In embodiments, the body is made of a plastics material. Such materials are easily selected by those of ordinary skill in the art, and include, in preferred embodiments, cellulose acetate butyrate, polypropylene, polyethylene, polyethylene terephthalate, and other flexible plastics. Co-extruded layers of different materials can provide desirable combinations of properties depending on the ultimate use and manufacturing process of the applicator. Exemplary materials are commercially available, e.g., as triple-layer co-extruded tubes such as those produced by Medi-Flex Hospital Products, Inc. (Overland Park, Kans.).

The material that comprises the ampoule is any material that is crushable or frangible, and that can be used to contain solid, liquid, or gaseous materials. In preferred embodiments, the crushable or frangible ampoule is made of glass or frangible plastics. Any suitable type of glass can be used to fabricate the ampoule, including, but not limited to, borosilicate glass and soda lime glass.

Compositions that can be contained within the ampoule and dispensed with the applicator are not particularly limited. Any material that a user desires to hold and dispense with the present applicator can be used, as long as the material is compatible with the materials used to fabricate the ampoule and the applicator body (and any other components of the applicator, such as the applicator tip, if present). Materials that can be held within the ampoule and dispensed with the applicator include gases, liquids, and solids.

Examples of gases include, but are not limited to, those of medical and industrial importance for verifying testing equipment, as well as initiators for chemical reactions, and gases that effect a biological response. Included in these types of gases are air, carbon monoxide (CO), methane ($CH_4$), hydrogen sulfide ($H_2S$), oxygen ($O_2$), and carbon dioxide ($CO_2$), as well as activators, reactants, stabilizers, and fragrances.

Examples of liquids include, but are not limited to, those applicable to medical, industrial, and home use. Included among these liquids are drugs, antiseptics, cleansers, solvents, dental products, adhesives, fragrances, and lubricants. Especially useful liquids include polymerizable liquid adhesives, such as the cyanoacrylate adhesives described in U.S. Pat. No. 5,928,611 and copending U.S. patent application Ser. No. 09/099,457, the disclosures of which are hereby incorporated by reference in their entireties.

Examples of solids include, but are not limited to, those that are dissolvable or dispersable in, or reactive with, liquids and gases, and those with medical, industrial, or home applications. Included among these types of solids are smelling salts, drugs, adhesives, cosmetics and other beauty or hygiene products.

The barrier material used as the protective coating can be any barrier material that is compatible with the materials comprising the applicator body and the ampoule and capable of adhering to or being affixed to the material of the ampoule and/or applicator body. To achieve such adherence or affixing, the ampoule may or may not be pretreated. When the barrier material is an adhesive, it can be applied as a pre-adhesive material (i.e., uncured) or as a cured adhesive. Examples of uncured adhesive materials include those materials that do not show strong adhesive properties, but can be converted into adhesives through chemical reactions, irradiation, or other types of interactions. For example, materials that polymerize upon irradiation or exposure to acids or bases can be used. Cured adhesives include adhesives that do not require further chemical reactions to impart an adhesive characteristic. Examples of cured adhesives include pressure sensitive adhesives such as those commonly applied to tapes or labels. Regardless of the state of the adhesive barrier material when it is applied, when used in the applicator of the invention, it should be cured at least to the point that it possesses the desired adhesive properties.

Adhesives useful in the invention include, but are not limited to, liquid adhesives. Exemplary suitable adhesives materials for use as the coating material include, but are not limited to, silicone room temperature vulcanization adhesives (RTVs), UV curable adhesives, hot melt adhesives, two-part adhesives (including epoxies), pressure sensitive adhesives, polymerizable adhesives (including cyanoacrylates), resins (including aliphatic resins), polyurethane, polyvinyl acetate, contact cements, and hide glues.

Included among the suitable adhesives are those adhesives with relatively low melting points. Also included are those that are liquid at room temperature (approximately 21–25° C.). For instance, the adhesive can be a liquid at an elevated temperature, for example 80° C., which cures at a lower temperature, such as room temperature. The adhesive can be applied to the exterior surface of the ampoule and allowed to cool to form the protective barrier on the ampoule. Alternately, the heated liquid adhesive can be applied to the interior surface of the applicator body, the ampoule can be inserted, and the adhesive allowed to cure by lowering the temperature. In such a situation, upon cooling of the applicator, the adhesive cures and forms the coating.

In embodiments, the interior surface of the applicator body can be coated or layered with a low melting point adhesive. Upon insertion of the ampoule into the applicator body, the applicator is heated to melt the low melting point adhesive. The applicator is then allowed to cool, allowing the adhesive to set up and form a protective barrier.

Similarly, as discussed above, the crushable ampoule can be coated with a low melting point adhesive. In this embodiment, upon insertion of the ampoule into the applicator body and heating of the applicator, the adhesive melts. Once the applicator is allowed to cool, the adhesive sets up and forms a protective barrier.

The applicator body 2 can also have a polymeric barrier material layer 7, such as a MYLAR® polyester label or film, affixed to or otherwise provided to cover portions of the exterior surface of the body 2 where fingers or the like will be used to crush the ampoule and may be otherwise subjected to glass shards from the crushed ampoule. The polymeric film is preferably clear to allow viewing of the contents of the ampoule and may be removable.

The barrier material 7 may also be a polymeric or plastic barrier layer coated onto a surface of the ampoule 6 itself, such as by dipping of the ampoule 6 into a non-cured liquid polymeric material, which upon subsequent drying or curing becomes coated on the surface of ampoule 6. Other known plastic coating techniques, using liquid, powder or solid polymeric materials can be used to apply the coating onto the ampoule surface.

The present invention also includes coextrusion of a flexible tube with an adhesive or polymeric protective material, wherein the adhesive or protective material is extruded such that it is located on the interior portion of the tube. Upon insertion of the crushable ampoule, the applicator can be heated, thus melting a low melting point adhesive or protective material. Upon cooling of the applicator, a protective coating is formed.

What is claimed is:

1. An applicator comprising:
   at least one crushable ampoule having an interior surface, an exterior surface, and a central portion, the crushable ampoule being crushable upon application of a force applied by a user's fingers,
   a flexible applicator body having a hollow lumen, said at least one crushable ampoule being located within said hollow lumen of said applicator body, and
   a polymeric barrier film disposed over an exterior surface of said flexible applicator body to cover at least the central portion of the at least one crushable ampoule where the predetermined force is applied and provide a physical barrier to penetration by shards created by crushing of the ampoule.

2. The applicator of claim 1, wherein said polymeric film is polyester.

3. The applicator of claim 1, wherein said polymeric film is transparent.

4. The applicator of claim 1, wherein the polymeric film is a tape or label.

5. A method of making an applicator, comprising:

providing at least one crushable ampoule having an exterior surface and an interior surface, the crushable ampoule being crushable upon application of a force applied by a user's fingers, providing a flexible applicator body having an open end, a closed end, and a hollow lumen, inserting said at least one crushable ampoule into said hollow lumen of said flexible applicator body, applying a polymeric barrier film over said exterior surface of said at least one crushable ampoule by applying said barrier film to an external surface of said flexible applicator body, wherein said barrier film protects against penetration of shards created during crushing of said at least one crushable ampoule.

6. The method of claim 5, wherein said polymeric barrier film is a polyester film.

7. The method of claim 6, wherein said polymeric film is transparent.

8. The method of claim 6, wherein said polyester film includes labeling indicia.

9. The method of claim 5, wherein said barrier material comprises a tape.

10. An applicator comprising:

at least one crushable ampoule having an interior surface, an exterior surface, and a central portion, a flexible applicator body having a hollow lumen, with said at least one crushable ampoule being located within said hollow lumen of said applicator body, and a clear polymeric barrier material disposed over an exterior surface of said flexible applicator body that protects an area where a force is applied by a user's fingers to break or crush the ampoule to protect the user's fingers from glass shards created during the break.

11. The applicator according to claim 10, wherein said barrier material is a polyester film.

* * * * *